United States Patent
Shotton et al.

(10) Patent No.: US 9,901,418 B2
(45) Date of Patent: Feb. 27, 2018

(54) ENDODONTIC INSTRUMENTS

(71) Applicant: DENTSPLY International Inc., York, PA (US)

(72) Inventors: Vincent Shotton, Broken Arrow, OK (US); Dan Ammon, Tulsa, OK (US)

(73) Assignee: DENTSPLY SIRONA, INC., York, PA (US)

( * ) Notice: Subject to any disclaimer, the term of this patent is extended or adjusted under 35 U.S.C. 154(b) by 262 days.

(21) Appl. No.: 14/311,134

(22) Filed: Jun. 20, 2014

(65) Prior Publication Data
US 2015/0216624 A1 Aug. 6, 2015

Related U.S. Application Data

(60) Provisional application No. 61/837,312, filed on Jun. 20, 2013.

(51) Int. Cl.
*A61C 5/02* (2006.01)
*A61C 5/42* (2017.01)

(52) U.S. Cl.
CPC .............. *A61C 5/023* (2013.01); *A61C 5/42* (2017.02)

(58) Field of Classification Search
CPC ............ A61C 5/023; A61C 5/025; A61C 5/42
USPC .......................................... 433/81, 102, 224
See application file for complete search history.

(56) References Cited

U.S. PATENT DOCUMENTS

| | | | | |
|---|---|---|---|---|
| 4,260,379 A | * | 4/1981 | Groves | A61C 5/023 408/210 |
| 4,443,193 A | * | 4/1984 | Roane | A61C 5/023 433/102 |
| 4,611,508 A | * | 9/1986 | Roane | A61C 5/023 76/119 |
| 6,299,445 B1 | * | 10/2001 | Garman | A61C 5/023 433/102 |
| 6,382,973 B2 | * | 5/2002 | Murai | A61C 5/023 433/102 |
| 6,712,611 B2 | * | 3/2004 | Garman | A61C 5/023 433/102 |
| 2001/0004518 A1 | * | 6/2001 | Murai | A61C 5/023 433/102 |
| 2003/0068597 A1 | * | 4/2003 | Garman | A61C 5/023 433/102 |
| 2004/0219485 A1 | * | 11/2004 | Scianamblo | A61C 5/42 433/102 |
| 2006/0216668 A1 | * | 9/2006 | Scianamblo | A61C 5/42 433/102 |

(Continued)

FOREIGN PATENT DOCUMENTS

| | | |
|---|---|---|
| EP | 0019356 A1 | 11/1980 |
| WO | 9937235 A2 | 7/1999 |
| WO | 0059399 A1 | 10/2000 |

*Primary Examiner* — Nicholas Lucchesi
(74) *Attorney, Agent, or Firm* — David A. Zdurne; Douglas J. Hura; Leana levin

(57) ABSTRACT

A rotatable endodontic file for cleaning/shaping a tooth root canal, comprising: an elongated shaft having a proximal end portion, a distal end and a tapered working portion having a rotational axis, the working portion extending from said proximal portion to said distal end; the external surface of said shaft working portion having a plurality of at least two spirals, a parallelogram-shaped cross section that has an axis of rotation that is asymmetric such that the center of mass (centroid) is not along the file axis.

8 Claims, 17 Drawing Sheets

(56) References Cited

U.S. PATENT DOCUMENTS

| | | | |
|---|---|---|---|
| 2006/0228668 A1* | 10/2006 | McSpadden | A61C 5/023 433/102 |
| 2006/0228669 A1* | 10/2006 | Scianamblo | A61C 5/023 433/102 |
| 2010/0167243 A1* | 7/2010 | Spiridonov | A61C 7/00 433/224 |
| 2015/0320517 A1* | 11/2015 | Rota | A61C 5/023 433/102 |

* cited by examiner

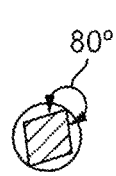 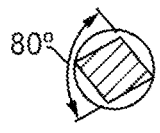  
FIG. 12A  FIG. 12B  FIG. 12C  FIG. 12D
   
FIG. 12E  FIG. 12F  FIG. 12G  FIG. 12H
   
FIG. 12I  FIG. 12J  FIG. 12K  FIG. 12L
  
FIG. 12M  FIG. 12N  FIG. 12O Chart 1.

Chart 2

Chart 3.

Chart 4.

ENDODONTIC INSTRUMENTS

CROSS-REFERENCE TO RELATED APPLICATIONS

This patent application claims the benefit of and priority to U.S. Provisional Patent Application Ser. No. 61/837,312, filed on Jun. 20, 2013, which are herein incorporated by reference for all purposes.

FIELD OF INVENTION

The present invention relates to endodontic instruments.

BACKGROUND OF THE INVENTION

Endodontic instruments can be used for cleaning and enlarging the endodontic cavity space ("ECS"), also known as the root canal system of a human tooth. The unprepared root canal is usually a narrow channel that runs through the central portion of the root of the tooth. Cleaning and enlargement of the ECS can be necessitated by the death or necrosis of the dental pulp, which is the tissue that occupies that space in a healthy tooth. This tissue can degenerate for a multitude of reasons, which include tooth decay, deep dental restorations, complete and incomplete dental fractures, traumatic injuries or spontaneous necrosis due to the calcification and ischemia of the tissue, which usually accompanies the ageing process. Similar to a necrotic or gangrenous appendix, the complete removal of this tissue is paramount, if not urgent, because of the subsequent development of infections or dental abscesses, septicemia, and even death.

The root canal system of a human tooth is often narrow, curved and calcified, and can be extremely difficult to negotiate or clean. Indeed, the conventional endodontic or root canal instruments currently available are frequently inadequate in the complete removal of the pulp and the efficient enlargement of the ECS. Furthermore, they are usually predisposed to breakage, causing further destruction to the tooth. Broken instruments are usually difficult, if not impossible to remove, often necessitating the removal of the tooth. Injury to the tooth, which occurs as the result of a frank perforation or alteration of the natural anatomy of the ECS, can also lead to failure of the root canal and tooth loss.

The unprepared root canal of the tooth usually begins as a narrow and relatively parallel channel. The portal of entry or the orifice and the portal of exit or foramen are relatively equal in diameter. To accommodate complete cleaning and filling of the canal and to prevent further infection, the canal must usually be prepared. The endodontic cavity preparation ("ECP") generally includes progressively enlarging the orifice and the body of the canal, while leaving the foramen relatively small. The result is usually a continuous cone-shaped preparation.

In general, endodontic instruments are used to prepare the endodontic cavity space as described above. Endodontic instruments can include hand instruments and engine driven instruments. The latter can but need not be a rotary instrument. Combinations of both conventional hand and engine-driven rotary instruments are usually required to perform an ECP successfully and safely.

An endodontic instrument may include a shaft that includes a tip and a shank. The endodontic instrument also includes grooves that spiral around the shaft. The grooves are referred to in the instant specification as flutes, (FIG. 1).

The cross section of a file shows flutes (FIG. 2).

The flutes are generally the spacing on both sides of a helical structure (or helix) that spirals around the shaft. The bottom portion of a flute—seen as a line or curve is referred to in the instant specification as a spline. The portion of a spline that comes into contact with a surface being cut during cutting will be referred to in the instant specification as a radial land.

A flute of an endodontic instrument usually includes a sharpened edge configured for cutting. Cutting Edge of FIG. 3 is an example of such a cutting edge.

Generally, an instrument having right-handed cutting edges is one that will cut or remove material when rotated clockwise, as viewed from shank to tip. In this specification, a direction of rotation will be specified as viewed from the shank to the tip of the instrument. The cut direction of rotation for a right handed endodontic instrument is clockwise. An instrument having left-handed cutting edges is one that will cut or remove material when rotated counter-clockwise. The cut direction of rotation, in this case, is counter-clockwise.

An endodontic instrument includes a working portion, which is the portion that can cut or remove material. The working portion is typically the portion along the shaft that is between the tip of the instrument and the shank end of the flutes. The working portion is also referred to in this specification as the cutting portion, and the working length as the cutting or working length.

Hand instruments are typically manufactured from metal wire blanks of varying sizes. The metallurgical properties of these wires, in general, have been engineered to produce a wide range of physical properties. These wires are usually then twisted or cut to produce specific shapes and styles. Examples of hand instruments include K-type, H-type, and R-type hand instruments. The barbed broach is manufactured from soft iron wire that is tapered and notched to form barbs or rasps along its surface. These instruments are generally used in the gross removal of pulp tissue or debris from the root canal system. Another R-type file is a rat-tail file.

K-type instruments in current usage include reamers and K-files. K files are generally available in carbon steel, stainless steel, and more recently, an alloy of nickel-titanium. To fabricate a K-type instrument, a round wire of varying diameters is usually grounded into three or four-sided pyramidal blanks and then rotated or twisted into the appropriate shapes. These shapes are specified and controlled by the American National Standards Institute ("ANSI") and the International Standards Organization ("ISO"). The manufacturing processes for reamers and files are similar; except however, files usually have a greater number of flutes per unit length than reamers. Reamers are used in a rotational direction only, whereas files can be used in a rotational or push-pull fashion. Files made from three-sided or triangular blanks have smaller cross sectional areas than files made from four-sided blanks. Thus, these instruments are usually more flexible and less likely to fracture. They also can display larger clearance angles and are more efficient during debridement. Triangular files, therefore, are generally considered more desirable for hand instrumentation.

H-type files are usually manufactured by grinding flutes into tapered round metal blanks to form a series of intersecting cones. H-type files can usually cut only in the pull direction (i.e., a pull stroke). Primarily because they have positive cutting angles, H-type files can be extremely efficient cutting instruments.

Hand instruments are usually manufactured according to guidelines of the ANSI and the ISO, which specified that a working portion of an instrument be 16 mm in length. ANSI and ISO further specified that a first diameter or $D_1$ of the instrument, be 1 mm from the tip or $D_0$. Other ANSI and ISO specifications require that: instruments have a standard taper of 0.02 mm per mm along the working portion; the tip maintains a pyramidal shape no greater than 75 degree. in linear cross section; and hand instruments are available in 21, 25, and 31 mm lengths.

In addition to the hand instruments described above, there are rotary instruments that are usually motor driven. G-type drills are usually available in carbon or stainless steel. As is typical, the G-type drill 300 shown includes a short flame-shaped head attached to a long shank. The flutes, in this instance, have U-shaped splines. The instrument includes cutting edges that have negative rake-angles. In general, a rake angle is the angle between the leading edge of a cutting tool and a perpendicular to the surface being cut. Rake angle is further described below. The flame-shaped head includes a non-cutting surface to prevent perforation. The instrument is usually used as a side-cutting instrument only. The instrument is relatively rigid and, therefore, may incur problem while used in a curved space, for example, the ECS.

The present invention discloses endodontic instruments having derivatives of parallelogram-shaped cross sections in an attempt to overcome the deficiencies of predicate endodontic files as well as files of U.S. Pat. No. 4,260,379, which discloses a preform parallelogram wire blank (spiral free) that is then twisted to create the spiral in the files.

SUMMARY OF INVENTION

The present invention seeks to improve upon prior root canal cleaning and/or enlarging systems by providing an improved rotatable endodontic file for cleaning/shaping a tooth root canal, comprising: an elongated shaft having a proximal end portion, a distal end and a tapered working portion having a rotational axis, the working portion extending from said proximal portion to said distal end; the external surface of said shaft working portion having a plurality of at least two spirals, a plurality of parallelogram-shaped cross sections along the working portion, each parallelogram-shaped cross sections having an acute angle and an axis of rotation that is centered such that the cross section center of mass (centroid) is located at the axis of rotation, wherein an acute angle of a first parallelogram-shaped cross section is different from an acute angle of a second parallelogram-shaped cross section.

In another aspect, the present invention contemplates a rotatable endodontic file for cleaning/shaping a tooth root canal, comprising: an elongated shaft having a proximal end portion, a distal end and a tapered working portion having a rotational axis, the working portion extending from said proximal portion to said distal end; the external surface of said shaft working portion having a plurality of at least two spirals, a plurality of parallelogram-shaped cross sections along the working portion, each parallelogram-shaped cross section having an acute angle and an axis of rotation that is asymmetric such that the center of mass (centroid) is not located at the axis of rotation, wherein an acute angle of a first parallelogram-shaped cross section is the same or different than an acute angle of a second parallelogram-shaped cross section of the working portion.

In another aspect, the present invention contemplates a rotatable endodontic file for cleaning/shaping a tooth root canal, comprising: an elongated shaft having a proximal end portion, a distal end and a tapered working portion having a rotational axis, the working portion extending from said proximal portion to said distal end; the external surface of said shaft working portion having a plurality of at least two spirals, a plurality of parallelogram-shaped cross sections along the working portion, at least one of the plurality of parallelogram-shaped cross sections two C-shaped or concave geometries along two symmetrical sides or four C-shaped or concave geometries along all four sides, each parallelogram-shaped cross section having an acute angle and a center of mass (centroid) that is located on the axis of rotation, each parallelogram-shaped cross section, wherein an acute angle of a first parallelogram-shaped cross section is different or the same as an acute angle of a second parallelogram-shaped cross section.

In another aspect, the present invention contemplates a rotatable endodontic file for cleaning/shaping a tooth root canal, comprising: an elongated shaft having a proximal end portion, a distal end and a tapered working portion having a rotational axis, the working portion extending from said proximal portion to said distal end; the external surface of said shaft working portion having a plurality of at least two spirals, a plurality of parallelogram-shaped cross sections that extend along the working portion, at least one of the parallelogram-shaped cross sections having one, two, three, or four C-shaped or concave geometries along one, two, three, or four sides, wherein each parallelogram-shaped cross section having an acute angle and a center of mass (centroid) is not located on the axis of rotation, and wherein an acute angle of a first parallelogram-shaped cross section is different or the same as an acute angle of a second parallelogram-shaped cross section.

In yet another aspect, any of the aspects of the present invention may be further characterized by one or any combination of the following features: wherein the acute angle of the first parallelogram-shaped cross section is towards the proximal end and is larger than the acute angle of the second parallelogram-shaped cross section that is towards the distal end; wherein the acute angles range between 50 degrees and 85 degrees, wherein the endodontic file is composed of a material selected from the group consisting of a Nitinol based material, a Cu based material, a titanium based material and a stainless steel based material; wherein the material is processed by high temperature, cold temperatures and/or strain; wherein the acute angle of the first parallelogram-shaped cross section is larger towards the proximal end than the acute angle of the second parallelogram-shaped cross section towards the distal end; wherein the acute angles range between 50 degrees and 85 degrees; wherein the acute angles of the first and second parallelogram-shaped cross sections range between 50 degrees and 85 degrees; wherein the material is processed by high temperature from about 100° C. to 600° C., 100° C. to 480° C., or about 100° C. to 180° C.; wherein the material is processed by cold temperature from about −100° C. to 10° C., −60° C. to 10° C., or about 0° C. to 10° C.; wherein the material is processed by strain and/or stress from about 1% to 10%, from about 2% to 9%, or from about 2% to 8%; wherein the acute angles decrease from the proximal end to the distal end and range between 50 degrees and 85 degrees, wherein a plurality of acute angles towards the proximal end are larger than a plurality of acute angles towards the distal end; wherein the a plurality of acute angles towards the proximal end are the same while being different than a plurality of acute angles towards the distal end; wherein the endodontic file is a variable tapered file; wherein the endodontic file is a constant tapered file; or any combination thereof.

It should be appreciated that the above referenced aspects and examples are non-limiting as others exist with the present invention, as shown and described herein. For example, any of the above-mentioned aspects or features of the invention may be combined to form other unique configurations, as described herein, demonstrated in the drawings, or otherwise.

BRIEF DESCRIPTION OF THE DRAWINGS

FIG. 12A is a first parallelogram-shaped cross section taken across 12A-12A of the endodontic file shown in FIG. 12.

FIG. 12B is a second parallelogram-shaped cross section taken across 12B-12B of the endodontic file shown in FIG. 12.

FIG. 12C is a third parallelogram-shaped cross section taken across 12C-12C of the endodontic file shown in FIG. 12.

FIG. 12D is a forth parallelogram-shaped cross section taken across 12D-12D of the endodontic file shown in FIG. 12.

FIG. 12E is a fifth parallelogram-shaped cross section taken across 12E-12E of the endodontic file shown in FIG. 12.

FIG. 12F is a sixth parallelogram-shaped cross section taken across 12F-12F of the endodontic file shown in FIG. 12.

FIG. 12G is a seventh parallelogram-shaped cross section taken across 12G-12G of the endodontic file shown in FIG. 12.

FIG. 12H is an eighth parallelogram-shaped cross section taken across 12H-12H of the endodontic file shown in FIG. 12.

FIG. 12I is a ninth parallelogram-shaped cross section taken across 12I-12I of the endodontic file shown in FIG. 12.

FIG. 12J is a tenth parallelogram-shaped cross section taken across 12J-12J of the endodontic file shown in FIG. 12.

FIG. 12K is an eleventh parallelogram-shaped cross section taken across 12K-12K of the endodontic file shown in FIG. 12.

FIG. 12L is a twelfth parallelogram-shaped cross section taken across 12L-12L of the endodontic file shown in FIG. 12.

FIG. 12M is a thirteenth parallelogram-shaped cross section taken across 12M-12M of the endodontic file shown in FIG. 12.

FIG. 12N is a fourteenth parallelogram-shaped cross section taken across 12N-12N of the endodontic file shown in FIG. 12.

FIG. 12O is a fifteenth parallelogram-shaped cross section taken across 12O-12O of the endodontic file shown in FIG. 12.

DETAILED DESCRIPTION OF THE INVENTION

Figure 1:
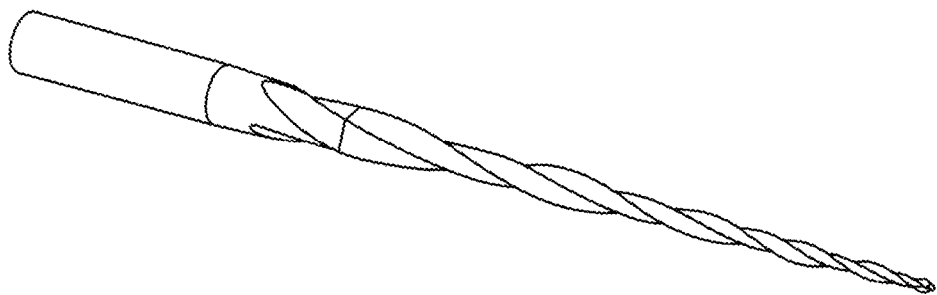
FIG. 1 is a perspective view of a first embodiment of an endodontic file of the present invention.
Figure 2:
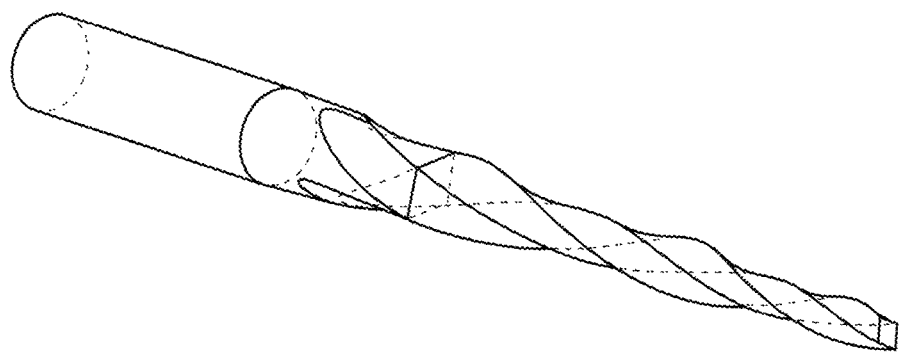
FIG. 2 is a perspective view of a second embodiment of an endodontic file of the present invention.
Figure 3:
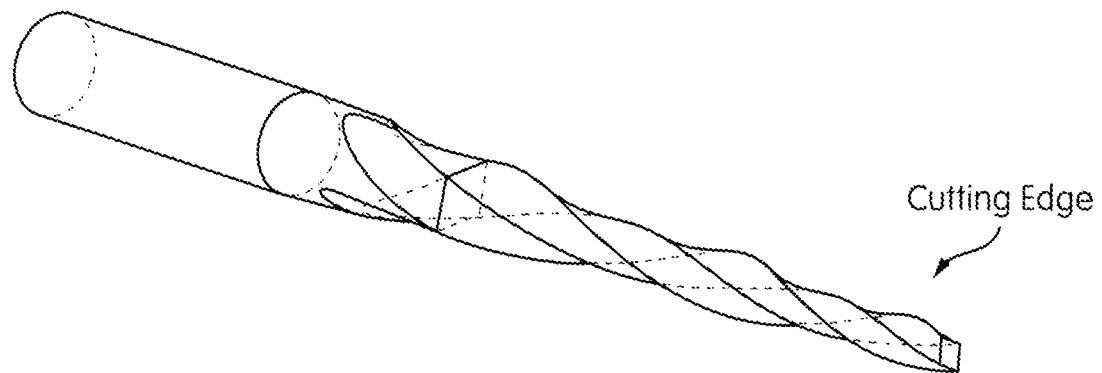
FIG. 3 is a perspective view of a third embodiment of an endodontic file of the present invention.
Figure 4:
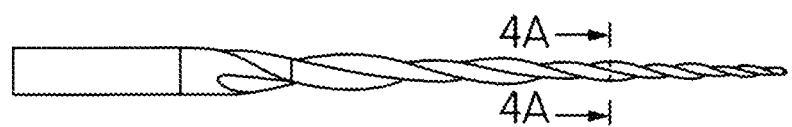
FIG. 4 is a perspective view of a forth embodiment of an endodontic file of the present invention.
Figure 4A:
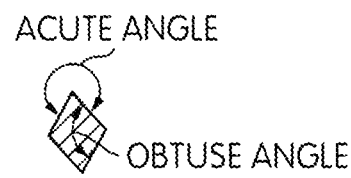
FIG. 4A is a parallelogram-shaped cross section taken across 4A-4A of the endodontic file shown if FIG. 4.

The invention discloses several novel approaches to parallelogram-shaped cross section and derivatives of parallelogram-shaped cross section for dental instruments (e.g., endodontic instruments such as endodontic files). In this invention, the angles of the parallelogram are ground directly into the file and the acute and obtuse angles of the parallelogram-shaped cross section vary along the axis of the file (FIG. 4).

Figure 5:
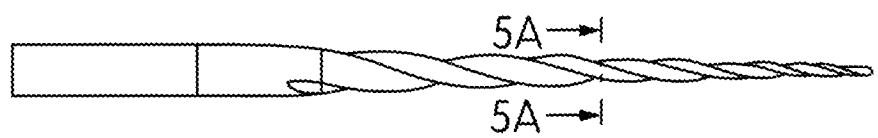
FIG. 5 is a perspective view of a fifth embodiment of an endodontic file of the present invention.
Figure 5A:
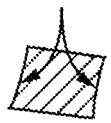
FIG. 5A is a parallelogram-shaped cross section taken across 5A-5A of the endodontic file shown in FIG. 5.

Another variation of the parallelogram-shaped cross section contains C-shaped or concave geometries along one, two, three or four sides of the parallelogram (FIG. 5).

The invention discloses several novel approaches to parallelogram-shaped cross sections and derivatives of parallelogram-shaped cross section for endodontic files.

Figure 6:
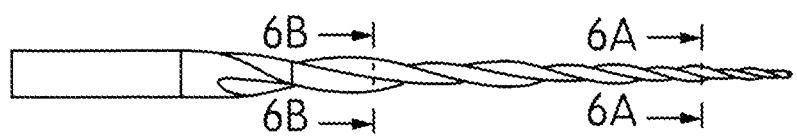
FIG. 6 is a perspective view of a sixth embodiment of an endodontic file of the present invention.
Figure 6A:
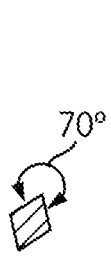
FIG. 6A is a first parallelogram-shaped cross section taken across 6A-6A of the endodontic file shown in FIG. 6.
Figure 6B:
FIG. 6B is a second parallelogram-shaped cross section taken across 6B-6B of the endodontic file shown in FIG. 6.

The first approach is a parallelogram-shaped cross section that has an axis of rotation that is centered such that the center of mass (centroid) is located at the axis of rotation. In this embodiment, the acute angle is different along the length of the file; preferably, the acute angle is larger at the tip and decreases as it approaches the shank. For example, the tip cross section has an acute angle of 70 degrees and decrease to an acute angle of 60 degrees as it approaches the shank (FIG. 6).

Figure 7:
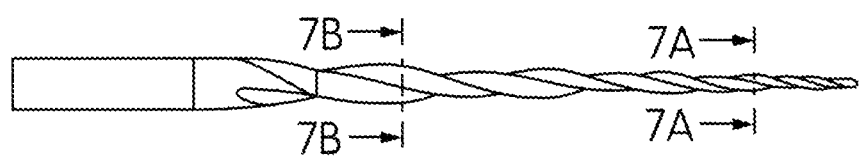
FIG. 7 is a perspective view of a seventh embodiment of an endodontic file of the present invention.
Figure 7A:
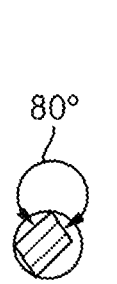
FIG. 7A is a first parallelogram-shaped cross section taken across 7A-7A of the endodontic file shown in FIG. 7.
Figure 7B:
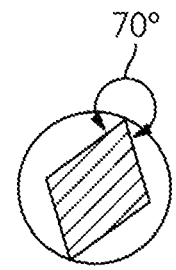
FIG. 7B is a second parallelogram-shaped cross section taken across 7B-7B of the endodontic file shown in FIG. 7.

The second approach is a parallelogram-shaped cross section that has an axis of rotation that is off-centered such that the center of mass (centroid) is not located at the axis of rotation. This is sometimes known as an asymmetric cross-section. In this embodiment the acute angle is different or the same along the length of the file. If the acute angle is different along the length of the file; preferably the acute angle is larger at the tip and decreases as it approaches the shank. For example, the tip cross section has an acute angle of 80 degrees and decreases to an acute angle of 70 degrees as it approaches the shank (FIG. 7).

Figure 8:
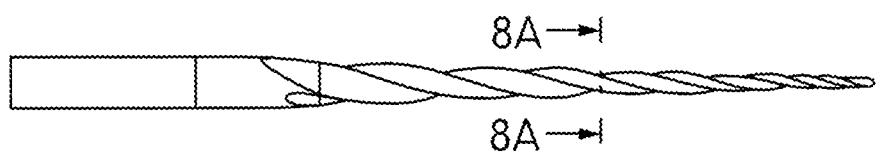
FIG. 8 is a perspective view of a eighth embodiment of an endodontic file of the present invention.
Figure 8A:
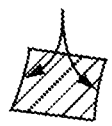
FIG. 8A is a parallelogram-shaped cross section taken across 8A-8A of the endodontic file shown in FIG. 8.

The third embodiment is a parallelogram-shaped cross section that has an axis of rotation that is centered such that the center of mass (centroid) is located at the axis of rotation and has 2 or 4 C-shaped or concave geometries along 2 symmetrical sides or all 4 sides of the cross section (FIG. 8).

Figure 9:
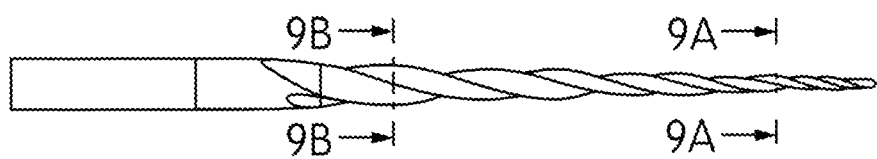
FIG. 9 is a perspective view of a ninth embodiment of an endodontic file of the present invention.
Figure 9A:
FIG. 9A is a first parallelogram-shaped cross section taken across 9A-9A of the endodontic file shown in FIG. 9.
Figure 9B:
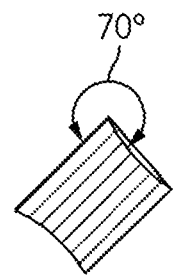
FIG. 9B is a second parallelogram-shaped cross section taken across 9B-9B of the endodontic file shown in FIG. 9.

In this embodiment the acute angle is different or the same along the length of the file. If the acute angles are different along the length of the file, preferably the acute angle is larger at the tip and decreases as it approaches the shank. For example, the tip cross section has an acute angle of 80 degrees and decrease to an acute angle of 70 degrees as it approaches the shank (FIG. 9).

Figure 10:
FIG. 10 is a perspective view of a tenth embodiment of an endodontic file of the present invention.
Figure 10A:
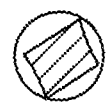
FIG. 10A is a parallelogram-shaped cross section taken across 10A-10A of the endodontic file shown in FIG. 10.

The fourth approach is a parallelogram-shaped cross section that has a cross section which is off-centered such that the center of mass (centroid) is not located at the axis of rotation (asymmetric cross-section) and has 1, 2, 3 or 4 C-shaped or concave geometries along 1, 2, 3 or 4 sides of the parallelogram (FIG. 10).

Figure 11:
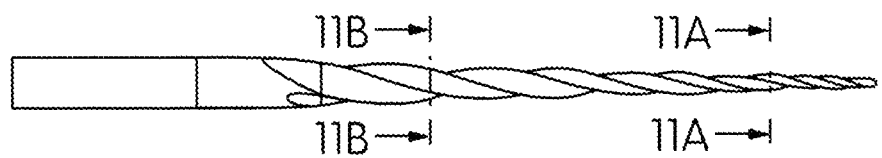
FIG. 11 is a perspective view of an eleventh embodiment of an endodontic file of the present invention.
Figure 11A:
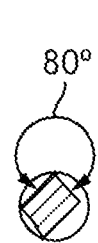
FIG. 11A is a first parallelogram-shaped cross section taken across 11A-11A of the endodontic file shown in FIG. 11.
Figure 11B:
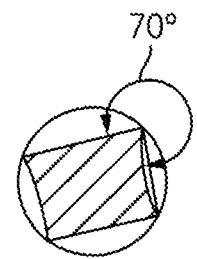
FIG. 11B is a second parallelogram-shaped cross section taken across 11B-11B of the endodontic file shown in FIG. 11.

In this embodiment the acute angle is different or the same along the length of the file. If the acute angle is different along the length of the file; preferably the acute angle is larger at the tip and decreases as it approaches the shank. For example, the tip cross section has an acute angle of 80 degrees and decrease to an acute angle of 70 degrees as it approaches the shank (FIG. 11).

It is contemplated that the angles located proximate to the tip portion may be at least about 60 degrees and preferably at least about 65 degrees. Furthermore, the angle proximate to the tip portion may be less than about 85 degrees, and preferably less than about 80 degrees. For example, the angles located proximate to the tip portion may range from about 60 to about 85 degrees and preferably from about 65 to about 80 degrees. It is further contemplated that the angles located distally (toward the shank) from the tip portion may be at least about 40 degrees and preferably at least about 50 degrees. Furthermore, the angle located distally (toward the shank) from the tip portion may be less than about 85 degrees, and preferably less than about 80 degrees. For example, the angles located distally (toward the shank) from the tip portion may range from about 40 to about 85 degrees and preferably from about 50 to about 80 degrees.

The lengths of the parallelogram (both on center and off center) may define various desirable ratios (e.g., from about 2:1 to about 1:4, from about 2:1 to about 1:2, from about 1:2 to about 1:1, from about 1:2 to about 4:5) of the helical angles between the acute angle helical angle and the obtuse angle helical angle, the helical angles between a first acute angle helical angle and an adjacent second acute angle helical angle, the helical angles between a first obtuse angle helical angle and an adjacent second obtuse angle helical angle, and/or the offset heights between the acute angle cutting edge and the obtuse angle cutting edge. It is appreciated that in one embodiment, the ratio of the lengths of the edges of the parallelogram may be about 1 (e.g., for the on center design) and/or, the ratio may range from about 1.6 to about 1.1 (e.g., for the off center parallelogram).

In another embodiment, the ratio of the acute angle helical angle and the obtuse angle helical angle may range from about 1.8 to about 1.2 (e.g., for the on center design) and/or the ratio may range from about 1.7 to about 1.1 (e.g., for the off center parallelogram).

In yet another embodiment, the offset heights between the acute angle cutting edge and obtuse angle cutting edge may vary from about 0.17 mm to about 0.05 mm (e.g., for the on center design), and/or the heights may vary from about 0.15 mm to about 0.1 mm (e.g., for the off center parallelogram).

Superelastic materials are typically metal alloys, which return to their original shape after substantial deformation. Examples of efforts in the art towards superelastic materials are found in U.S. Pat. No. 6,149,501, which is herein incorporated by reference for all purposes.

The endodontic instruments disclosed above can be made of shape memory alloys (e.g., NiTi based, Cu based, Fe based, or combinations thereof) in their martensitic state of the present invention may provide more flexibility and increase fatigue resistance by optimized microstructure, which is particularly effective in shaping and cleaning canals with severe curvatures. Superelastic alloys such as nickel titanium (NiTi) or otherwise can withstand several times more strain than conventional materials, such as stainless steel, without becoming plastically deformed.

This invention relates to dental instruments disclosed above. Specifically, this invention relates to endodontic rotary instruments for use in root canal cleaning and shaping procedures. The present invention provides an innovation of endodontic instrument that is made of shape memory alloys (SMA) such as Nickel-Titanium (NiTi) based systems, Cu based systems Fe based systems, or any combination thereof (e.g., materials selected from a group consisting of near-equiatomic Ni—Ti, Ni—Ti—Nb alloys, Ni—Ti—Fe alloys, Ni—Ti—Cu alloys, beta-phase titanium and combinations thereof).

The present invention comprises rotary instruments made of NiTi Shape Memory Alloys, which provide one or more of the following novel aspects:

Primary metallurgical phase in microstructure: martensite is the primary metallurgical phase in the present invention instrument, which is different from standard NiTi rotary instruments with predominant austenite structure at ambient temperature.

Higher austenite finish temperature (the final $A_f$ temperature measured by Differential Scanning calorimetry): the austenite finish temperature is preferably higher (e.g., at least about 3.degree. C.) than the ambient temperature (25.degree. C.); in contrast, most standard superelastic NiTi rotary instruments have austenite finish temperatures lower than ambient temperature.

Due to higher austenite finish temperature, the present invention instrument would not return to the original complete straight state after being bent or deflected; in contrast, most standard superelastic NiTi rotary instruments can return to the original straight form via reverse phase transformation (martensite-to-austenite) upon unloading.

Endodontic instruments made of NiTi shape memory alloys in their martensitic state have significantly improved overall performance than their austenitic counterparts (regular superelastic NiTi instruments), especially on flexibility and resistance against cyclic fatigue.

The strength and cutting efficiency of endodontic instruments can also be improved by using ternary shape memory alloys NiTiX (X: Co, Cr, Fe, Nb, etc) based on the mechanism of alloy strengthening.

Specifically, the present invention instrument has essential and most desired characteristics for successful root canal surgery, including higher flexibility and lower stiffness, improved resistance to cyclic fatigue, higher degree of rotation against torsional fracture, more conforming to the shape of highly curved canals (less likely for ledging or perforation), and minimum possibility of instrument separation in comparison against conventional endodontic instruments made of NiTi shape memory alloy in superelastic condition with fully austenitic phase in microstructure.

Example #1 (on Center File Designs)

30.06 ISO Tapered files were manufactured with parallelogram-shaped cross sections with constant angles (e.g., constant acute angles generally throughout the working portion of the file). Table 1 provides the measured cutting efficiency for the on center file designs of these tapered files with parallelogram-shaped cross sections with constant angles as compared to a triangle cross section ISO Tapered file (Vortex) . . . .

TABLE 1

| File | Average Cutting Efficiency (mm/sec) | Was it more efficient than 30.06 Vortex? |
| --- | --- | --- |
| 80 Deg. 30.06 | 0.304 | No |
| 70 Deg. 30.06 | 0.443 | Yes (by about 10%) |
| 60 Deg. 30.06 | 0.477 | Yes (by about 17%) |
| 65 Deg. 30.06 | 0.455 | Yes (by about 11%) |
| 75 Deg. 30.06 | 0 387 | Statistically the same |
| Vortex 30.06 (60 Deg) | 0.403 | |

Figure 14:
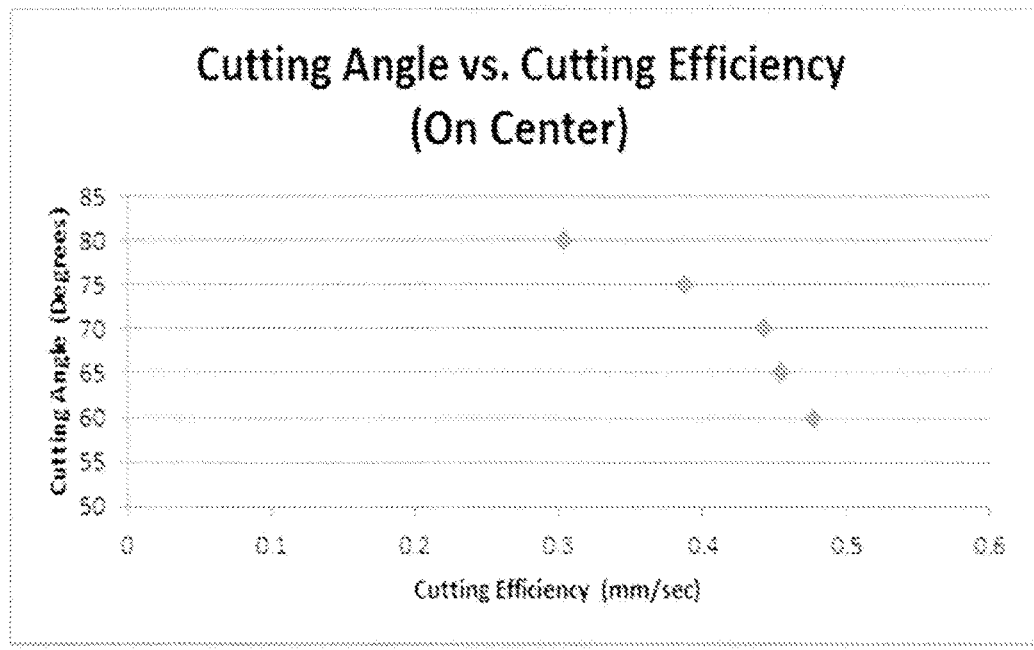
FIG. 14 is a first chart showing Cutting Angle versus Cutting Efficiency.
Figure 15:
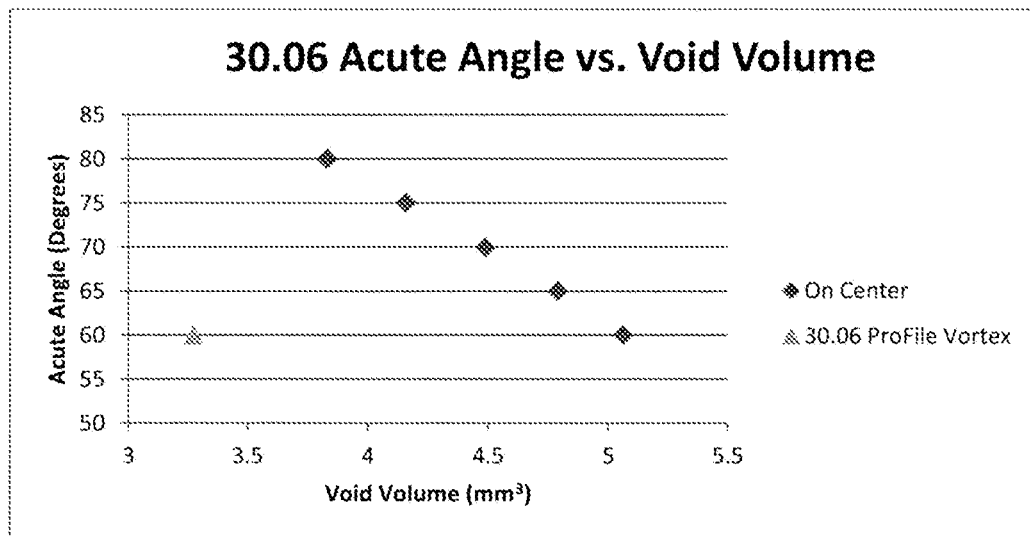
FIG. 15 is a second chart showing Acute Angle of a File on Center versus Void Volume.
Figure 16:
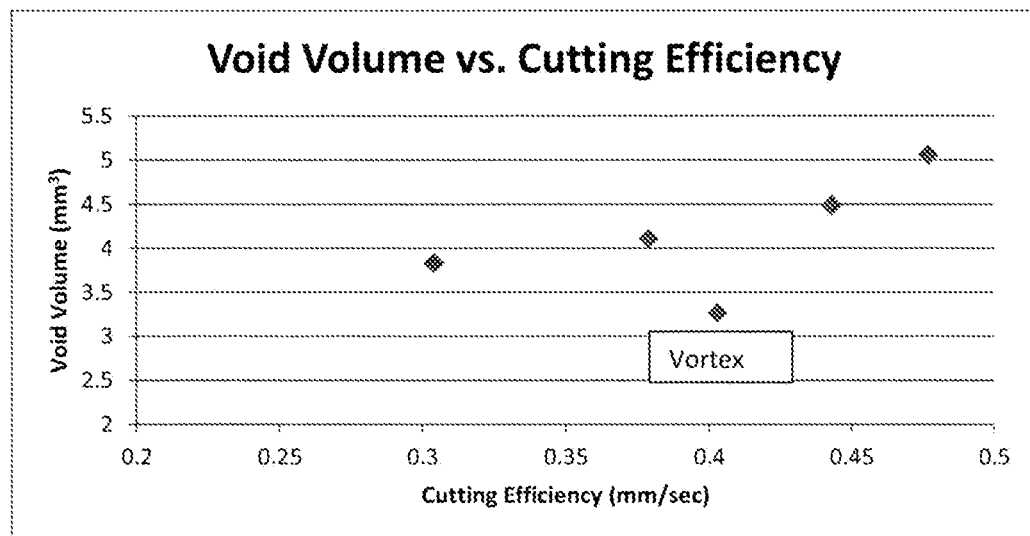
FIG. 16 is a third chart showing Void Volume versus Cutting Efficiency.

As shown in Table 1 and Charts 1-3 (FIGS. 14-16) for endodontic files having parallelogram-shaped cross sections with constant angles (generally throughout the working portion of the file), the smaller the parallelogram angle resulted in higher the void volume and higher cutting efficiency. The definition of void volume is the amount of free volume between the file and the canal wall.

Example #2 (on Center File Designs)

Figure 12:
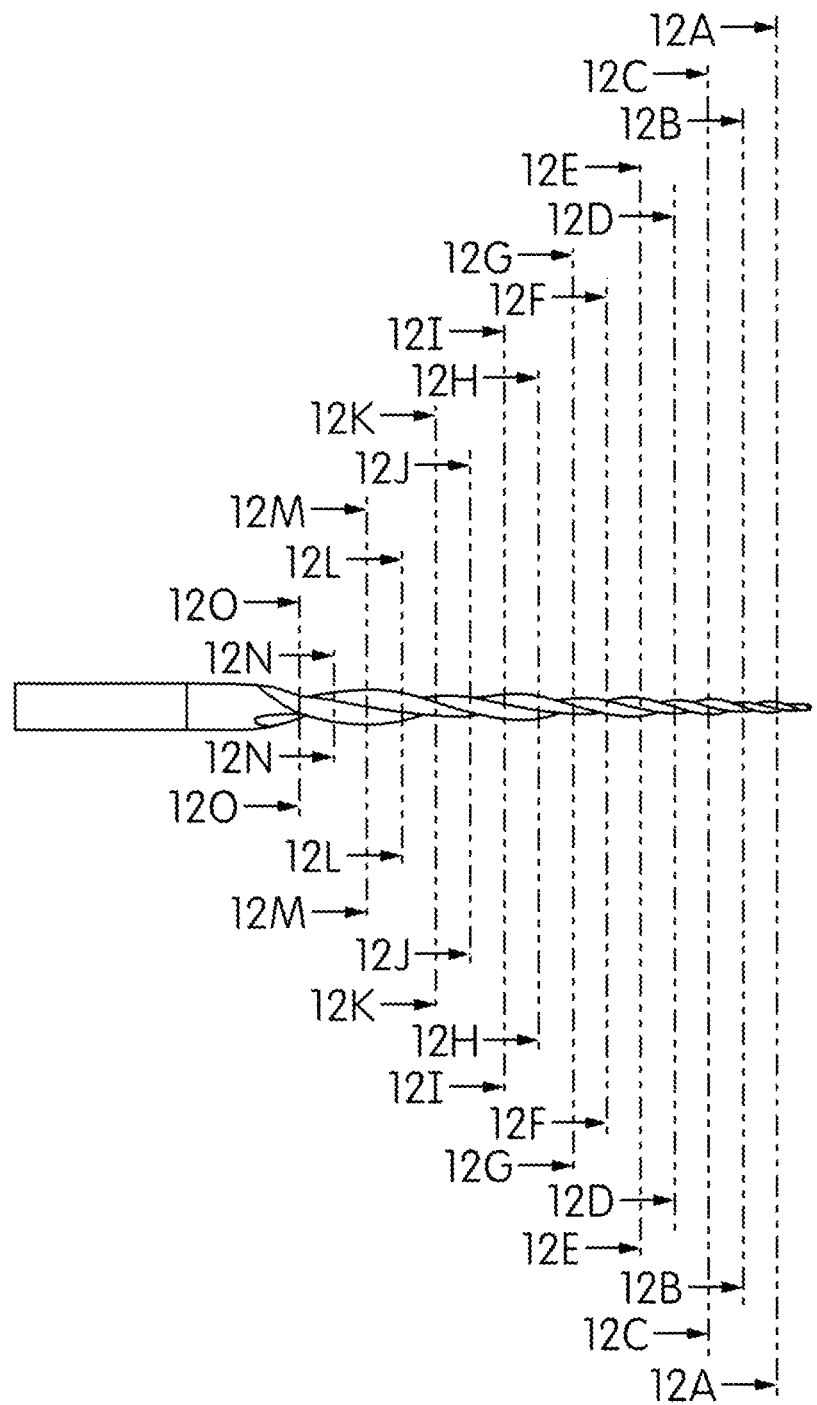
FIG. 12 is a perspective view of a twelfth embodiment of an endodontic file of the present invention.

30.06 ISO tapered files were manufactured with parallelogram-shaped cross sections with variable angles (e.g., variable acute angles, generally throughout the working portion of the file). Table 2 provides measured cutting efficiency for on center file designs of 30.06 ISO Tapered files, which were manufactured with parallelogram-shaped cross sections having variable angles as compared to a triangle cross section ISO Tapered file (Vortex). FIG. 12 provides an example of one of the endodontic files having a parallelogram-shaped cross sections with variable angles (generally throughout the working portion of the file)

TABLE 2

| Design | Average Cutting Efficiency (mm/sec) |
| --- | --- |
| M4 30.06 80-70 deg. | 0.333 |
| M4 30.06 80-60 deg. | 0.432 |
| M4 30.06 70-60 deg. | 0.391 |
| M4 30.06 70-50 deg. | 0.450 |
| 30.06 Vortex | 0.403 |

As shown in Table 2: for endodontic files having parallelogram-shaped cross sections with variable angles (generally throughout the working portion of the file), larger cross section angles results in higher cutting efficiency (with the exception of higher angles apically). Furthermore, it is appreciated that larger cross section angles at the tip of the file may reduce void volume while providing more mass at the tip to increase the strength of the file (which reduces file breakage). Desirably, endodontic files having parallelogram-shaped cross sections with variable angles (generally throughout the working portion of the file) include larger cross section angles at or towards the tip portion and lower cross section angles towards the shank.

Example #3 (Off Center File Designs)

30.06 ISO Tapered files were manufactured with parallelogram-shaped cross sections with constant angles and compared to a triangle cross section ISO Tapered file for cutting efficiency.

Figure 13:
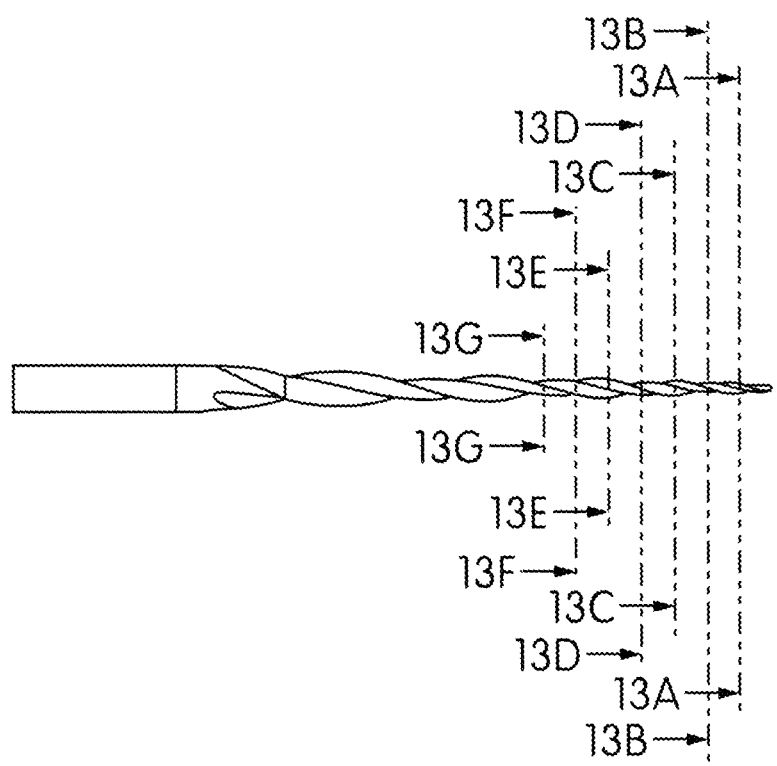
FIG. 13 is a perspective view of an eleventh embodiment of an endodontic file of the present invention.
Figure 13A:
FIG. 13A is a first parallelogram-shaped cross section taken across 13A-13A of the endodontic file shown in FIG. 13.
Figure 13B:
FIG. 13B is a second parallelogram-shaped cross section taken across 13B-13B of the endodontic file shown in FIG. 13.
Figure 13C:
FIG. 13C is a third parallelogram-shaped cross section taken across 13C-13C of the endodontic file shown in FIG. 13.
Figure 13D:
FIG. 13D is a forth parallelogram-shaped cross section taken across 13D-13D of the endodontic file shown in FIG. 13.
Figure 13E:
FIG. 13E is a fifth parallelogram-shaped cross section taken across 13E-13E of the endodontic file shown in FIG. 13.
Figure 13F:
FIG. 13F is a sixth parallelogram-shaped cross section taken across 13F-13F of the endodontic file shown in FIG. 13.
Figure 13G:
FIG. 13G is a seventh parallelogram-shaped cross section taken across 13G-13G of the endodontic file shown in FIG. 13.
Figure 17:
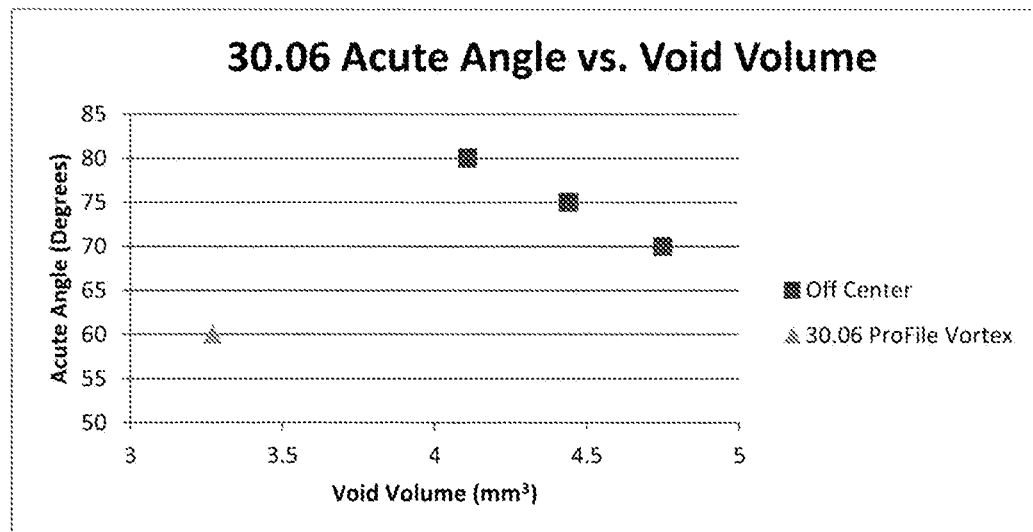
FIG. 17 is a fourth chart showing Acute Angle of a File Off Center versus Void Volume.
Figure 18:
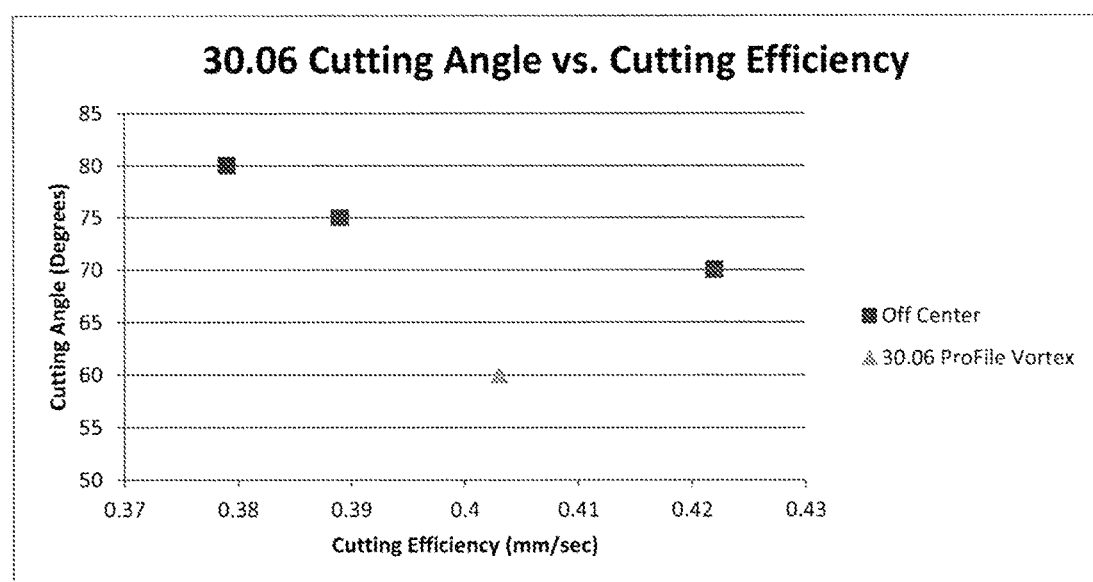
FIG. 18 is a first chart showing Cutting Angle of a File Off Center versus Cutting Efficiency.

As shown in Charts 4-5 (FIGS. 17-18) for off center file designs of 30.06 ISO Tapered files, which were manufactured with parallelogram-shaped cross sections having constant angles, smaller cross section angles results in higher cutting efficiency and higher void volume. FIG. 13 provides an example of one of the endodontic files (off center file design) having a parallelogram-shaped cross sections with constant angles (generally throughout the working portion of the file).

Method of Manufacturing

Examples of efforts in the art directed to methods of manufacturing endodontic instruments may be found in, but not limited to U.S. Patent Application 20110271529, which is herein incorporated by reference for all purposes.

It will be appreciated that functions or structures of a plurality of components or steps may be combined into a single component or step, or the functions or structures of one-step or component may be split among plural steps or components. The present invention contemplates all of these combinations. Unless stated otherwise, dimensions and geometries of the various structures depicted herein are not intended to be restrictive of the invention, and other dimensions or geometries are possible. In addition, while a feature of the present invention may have been described in the context of only one of the illustrated embodiments, such feature may be combined with one or more other features of other embodiments, for any given application. It will also be appreciated from the above that the fabrication of the unique structures herein and the operation thereof also constitute methods in accordance with the present invention. The present invention also encompasses intermediate and end products resulting from the practice of the methods herein. The use of "comprising" or "including" also contemplates embodiments that "consist essentially of" or "consist of" the recited feature.

The explanations and illustrations presented herein are intended to acquaint others skilled in the art with the invention, its principles, and its practical application. Those skilled in the art may adapt and apply the invention in its numerous forms, as may be best suited to the requirements of a particular use. Accordingly, the specific embodiments of the present invention as set forth are not intended as being exhaustive or limiting of the invention. The scope of the invention should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes.

The invention claimed is:

1. A rotatable endodontic file for cleaning/shaping a tooth root canal, comprising: an elongated shaft having a proximal end, a proximal end portion, a distal end and a tapered working portion having a file axis, the working portion extending from said proximal end portion to said distal end; an external surface of said shaft working portion being defined by at least two spirals that define at least two opposing curved side walls of a plurality of parallelogram-shaped cross sections along the working portion, at least two of the plurality of parallelogram-shaped cross sections having an acute angle and an axis of rotation that is asymmetric such that a center of mass is not along the file axis, wherein a first parallelogram-shaped cross section has a first center of mass and a second parallelogram-shaped cross section has a second center of mass being different from the first center of mass of said first parallelogram-shaped cross section, both the first center of mass of the first parallelogram-shaped cross section and the second center of mass of the second parallelogram-shaped cross section are not along the file axis.

2. An endodontic file according to claim 1, wherein the first parallelogram-shaped cross section has an acute angle that is larger towards the proximal end portion than an acute angle of the second parallelogram-shaped cross section towards the distal end.

3. An endodontic file according to claim 2, wherein the acute angles range between 50 degrees and 85 degrees.

4. An endodontic file according to claim 1 wherein the acute angles range between 50 degrees and 85 degrees.

5. An endodontic file according to claim 1, wherein the file is composed of a material selected from the group consisting of a Nitinol based material, Cu based material, titanium based material and a stainless steel based material.

6. An endodontic file according to claim 5, wherein the material is processed by high temperature, cold temperatures and/or strain.

7. An endodontic file according to claim 1, wherein the endodontic file is a variable tapered file.

8. An endodontic file according to claim 1, wherein the endodontic file is a constant tapered file.

* * * * *